US012806039B2

(12) United States Patent
Wills et al.

(10) Patent No.: US 12,806,039 B2
(45) Date of Patent: Nov. 24, 2026

(54) DEVICE FOR DISASSEMBLING IMPLANT SYSTEMS

(71) Applicant: Encore Medical, L.P., Austin, TX (US)

(72) Inventors: Kevin Michael Wills, Austin, TX (US); Annika Westerberg, Austin, TX (US); Heather Fewell, Spring, TX (US)

(73) Assignee: Encore Medical, L.P., Austin, TX (US)

( * ) Notice: Subject to any disclaimer, the term of this patent is extended or adjusted under 35 U.S.C. 154(b) by 858 days.

(21) Appl. No.: 18/060,722

(22) Filed: Dec. 1, 2022

(65) Prior Publication Data

US 2023/0181337 A1 Jun. 15, 2023

Related U.S. Application Data

(60) Provisional application No. 63/265,475, filed on Dec. 15, 2021.

(51) Int. Cl.
*A61F 2/46* (2006.01)
*A61B 17/16* (2006.01)

(52) U.S. Cl.
CPC ........ *A61F 2/4609* (2013.01); *A61B 17/1637* (2013.01)

(58) Field of Classification Search
CPC . A61F 2/4609; A61B 17/164; A61B 17/1642; A61B 17/1637
See application file for complete search history.

(56) References Cited

U.S. PATENT DOCUMENTS

| | | | | |
|---|---|---|---|---|
| 7,572,294 | B2 * | 8/2009 | Meridew | A61F 2/4637 623/22.12 |
| 7,785,331 | B2 | 8/2010 | Leisinger et al. | |
| 11,103,367 | B2 | 8/2021 | Wills et al. | |
| 11,452,620 | B2 | 9/2022 | Furore et al. | |
| 2019/0388243 | A1 * | 12/2019 | Furore | A61F 2/4637 |

OTHER PUBLICATIONS

International Search Report and Written Opinion dated Mar. 9, 2023 in application No. PCT/US2022/051635.

* cited by examiner

*Primary Examiner* — Kevin T Truong
*Assistant Examiner* — Diana Jones
(74) *Attorney, Agent, or Firm* — Eversheds Sutherland (US) LLP

(57) ABSTRACT

A device for separating a hard acetabular liner (e.g., metal, ceramic, etc.) positioned in an acetabular shell, the device including an elongated member having a proximal and distal end, an engagement structure positioned at the proximal end of the elongated member. The engagement structure includes a first portion having a curved outer surface, a first end-face aligned substantially perpendicular to the longitudinal axis of the device, and an inner surface extending from the first end-face, the first portion structured to fit at least partially into a scallop-shaped recess on a peripheral top surface of the acetabular shell, and further includes a second portion separated from the first portion by an opening, structured to accept the top surface of the acetabular liner, and including an outer surface extending a second length from the proximal end of the elongated member, structured to contact the top surface of the acetabular shell.

20 Claims, 6 Drawing Sheets

DEVICE FOR DISASSEMBLING IMPLANT SYSTEMS

REFERENCE TO PRIORITY APPLICATIONS

This application claims the benefit of U.S. Provisional Application No. 63/265,475, filed Dec. 15, 2021. Any and all applications for which a foreign or domestic priority claim is identified in the Application Data Sheet as filed with the present application are hereby incorporated by reference under 37 CFR 1.57.

TECHNICAL FIELD

This disclosure generally relates to disassembling multi-component implant systems. More specifically, this disclosure relates to devices and methods for mechanically decoupling an acetabular liner coupled to a shell.

BACKGROUND

In implant systems, a relatively sharp tool can be used for removing or revising the implant, for example, de-coupling an acetabular liner coupled to an acetabular cup (acetabular liner). In some embodiments, the liners may comprise material that is not exceptionally hard and can be damaged (for example, a polyethylene liner). However, some configurations can provide a unique challenge due to the configuration such that a universal tool cannot be used to separate the liner from the acetabular cup, especially without damaging the liner. Also, some configurations of an implant assembly provides a unique challenge because a metal liner is submerged into, and taper locked into, the acetabular cup. Accordingly, it would be advantageous to have a better tool that allows the liner to be separated from the acetabular cup without damaging the acetabular cup or the liner.

SUMMARY OF THE INVENTION

The devices, systems, and methods of the present disclosure have several features, no single one of which is solely responsible for its desirable attributes. Without limiting the scope of this invention as expressed by the claims which follow, certain innovations will now be discussed briefly. After considering this discussion, and other sections provided herein, one will understand how the features of embodiments of the disassembly instrument and methods of using the disassembly instrument in this disclosure to de-coupling hard bearing acetabular liners (e.g., metal, ceramic, etc.) coupled to a shell provide several advantages.

One innovation includes a disassembly device for separating a acetabular liner positioned in and coupled to a shell. The disassembly device can include an elongated member having a distal end and a proximal end, and a longitudinal axis extending between the distal end and the proximal end; an engagement structure at the proximal end of the elongated member, the engagement structure having a frustum-shaped outer surface including a first portion and a second portion separated by an opening defined in-part by a curved inside surface having a distal portion. The first portion includes a curved outer surface extending a first length from the proximal end of the elongated member, a first end face aligned substantially perpendicular with respect to the longitudinal axis, and an inner surface extending from the first end face to the curved inside surface wherein the first portion is structured to fit at least partially into a scallop-shaped recess on a peripheral top surface of the acetabular shell. The second portion includes a curved outer surface extending a second length from the proximal end of the elongated member where the second length is less than the first length, a second end face aligned substantially perpendicular with respect to the longitudinal axis, and an inner surface aligned substantially perpendicular to the second face and extending from the second end face to the curved inside surface.

Various embodiments can include additional features. In some embodiments, the first portion is structured and sized to fit at least partially into a scallop-shaped recess on a peripheral top surface of the acetabular shell. In some embodiments, the first end-face is hemispherical-shaped. In some embodiments, the second end-face is hemispherical-shaped. In some embodiments, the frustum-shaped outer surface tapers inward at an angle A relative to the longitudinal axis as it extends away from the proximal end of the elongated member, wherein angle A is between about 0 and about 20 degrees. In some embodiments, angle A is between about 5 degrees and about 11 degrees. In some embodiments, the inner surface extends at an angle C which is between about 30 degrees and about 88 degrees. In some embodiments, angle C is between about 50 degrees and about 80 degrees. In some embodiments, the first length is between about 4 mm and about 9 mm. In some embodiments, the first length is about 6 mm, plus or minus 1 mm. In some embodiments, the second length is between about 2 mm and about 7 mm. In some embodiments, the second length is about 3.5 mm, plus or minus 1 mm. In some embodiments, the curved inside surface is U-shaped. In some embodiments, the first end-face surface includes a straight edge and a curved edge, and the straight edge of the first end-face surface is between about 4.5 mm and about 6.6 mm in length. In some embodiments, the second end-face surface includes a straight edge and a curved edge, and the straight edge of the second end-face surface is between about 3 mm and about 5 mm in length. In some embodiments, the disassembly device further includes a handle positioned on the distal end of the elongated member. In some embodiments, the elongated member is a rod having a circular cross-sectional area. In some embodiments, the acetabular liner comprises metal. In some embodiments, the acetabular liner comprises ceramic.

Another innovation includes a disassembly device for separating a hard bearing acetabular liner positioned in, and coupled to a shell. The disassembly device comprising: an elongated member having a distal end and a proximal end, and a longitudinal axis extending between the distal end and the proximal end; an engagement structure at the proximal end of the elongated member, the engagement structure comprising a first portion and a second portion separated by an opening, the first portion comprising a curved outer surface extending a first length from the proximal end of the elongated member, a first end face aligned substantially perpendicular with respect to the longitudinal axis, wherein the first portion is structured to fit at least partially into a scallop-shaped recess on a peripheral top surface of the acetabular shell; a second portion comprising an outer surface extending a second length from the proximal end of the elongated member, a second end face aligned substantially perpendicular with respect to the longitudinal axis, and wherein the second portion is structured to contact the top surface of the acetabular shell; and an opening separating the first and second portion comprising inner surfaces extending from first end face and second end face to the inside surface. Further, the opening of the disassembly device is structured to accept the top surface of the acetabular liner and allowing the first portion of the device to be positioned within the inner surface of the liner, while the second portion is contact with the top surface of the acetabular shell, without contacting the liner. In various embodiments, the liner comprises metal or ceramic.

Another innovation includes a method of separating a liner from an acetabular shell, the method comprising: providing a disassembly tool, the disassembly tool including an elongated member having a distal end and a proximal end, and a longitudinal axis extending between the distal end and the proximal end; an engagement structure at the proximal end of the elongated member, the engagement structure comprising a first portion and a second portion separated by an opening, the first portion comprising a curved outer surface extending a first length from the proximal end of the elongated member, and a first end face aligned substantially perpendicular with respect to the longitudinal axis, and the second portion comprising an outer surface extending a second length from the proximal end of the elongated member, and a second end face aligned substantially perpendicular with respect to the longitudinal axis, and wherein the second portion is structured to contact the top surface of the acetabular shell; and an opening separating the first and second portion, the opening defined by an inner surface extending from first end face and second end face; positioning the top surface of the acetabular liner in the opening with the first portion of the device positioned adjacent to an inner surface of the liner and the second portion is contact with the top surface of the acetabular shell without contacting the liner; and providing a sudden force on the distal end of the elongated member along the longitudinal axis in the direction of the proximal end to at least partially separate the shell from the liner.

BRIEF DESCRIPTION OF THE DRAWINGS

The features and advantages of the devices and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

FIG. 3A shows a left-side elevation view of the instrument, FIG. 3B shows the bottom-side elevation view of the instrument, FIG. 3C shows the right-side elevation view of the instrument, and FIG. 3D shows a top elevation view of the instrument.

DETAILED DESCRIPTION

Figure 1:
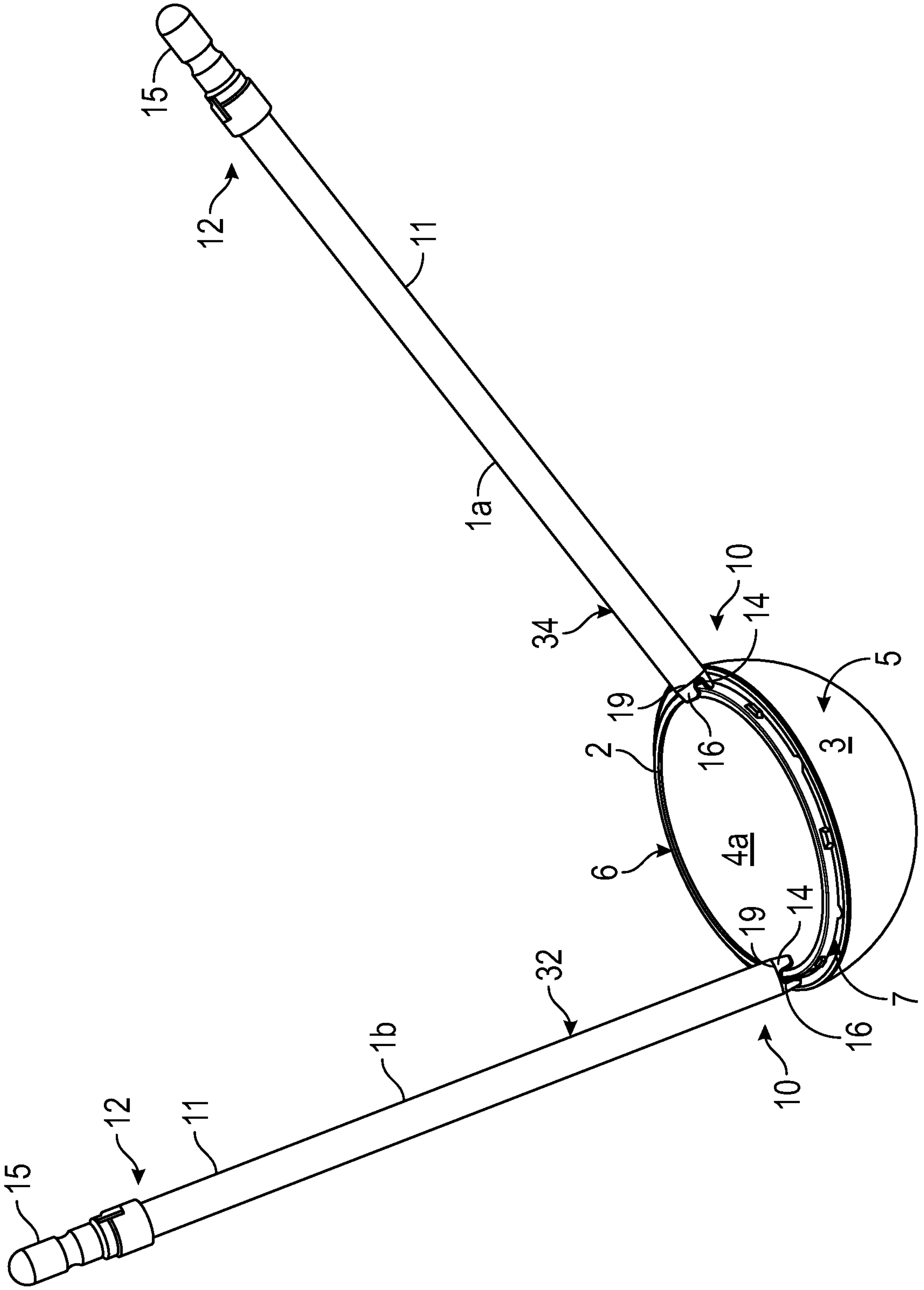
FIG. 1 illustrates an example of two disassembly instruments positioned to separate an acetabular liner from an acetabular cup, the acetabular liner being positioned inside the acetabular cup. The example of a disassembly instrument illustrated in this disclosure may be referred to herein as a “disassembly instrument,” “disassembly device,” or simply the “instrument” or “device” for ease of reference.

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, a device for disassembling an implant system, comprising a liner from a shell, or a method of disassembling an implant system maybe practiced, using any number of the aspects set forth herein. In addition, disclosed devices may be implemented, or such a method may be practiced, using other structure, functionality, or structure and functionality in addition to, or other than one or more of the aspects set forth herein.

Overview of Technology

Most implant systems provide a method for removing or revising the implant. The dual mobility implant assembly provides a unique challenge because the metal liner is submerged into and taper locked into the cup. There are limited features exposed in the liner to help with removal and the liner cannot be pierced (like a poly liner). The disclosed disassembly instrument is an instrument with unique features that take advantage of some features of the implant liner to facilitate separating a liner from a shell that is coupled to the liner.

Referring generally to the example of the removal instrument 1 illustrated in FIGS. 1-9, in one use the removal instrument 1 can be used to remove a liner 2 from a shell 3 by providing structure to impact the shell 3 to shock/vibrate the liner 2 free from the shell 3. The instrument 1 includes an elongated member 11 having a proximal end 10 with an engagement structure 19 that is used to contact the liner 2 in the shell 3. The instrument 1 also has a distal end 12 that includes a handle 15, or feature that allows coupling to a handle, that can be used as an impact portion to provide a sudden and/or jarring force from the handle 15 through the elongated member 11 and through the engagement structure 19, to communicate the sudden and/or jarring force to the shell 3. Such a force can be applied to the handle 15 by a user's hand or a tool (e.g., a hammer). The engagement structure 19 has a cut or slot (e.g., opening 13) that straddles the protruding rim of the liner 2, and a second portion 16 of the engagement structure 19 can firmly contact the shell 3. This provides an advantage because the slot keeps the removal instrument located on the rim of the cup during impaction, instead of bouncing off or skiving. Competitive systems may have some sort of a removal instrument that impacts the face of the cup, but they do not have an engagement structure with the described first portion 14 and second portion 16 with an opening 13 between them that allows the engagement structure 19 to firmly engage the liner 2 or the shell 3, and decouple the liner 2 from the shell 3.

In a second aspect, the removal instrument 1 can be used to impact the liner 2 and shock/vibrate the liner 2 free from the shell 3. In some embodiments, one side (e.g., a first portion 14 of the engagement structure 19) of the removal instrument 1 is shaped to conform within one the empty scallop cutouts 9 in the cup 3. In an example, a dual mobility implant liner can have six outward scallops, instead of 12 like the poly liner. In another example, a liner can have fewer scallop protrusions than scallop recesses in the cup, which means that some of the recesses will not be filled. In some examples, this means that there may be six scallop cut-outs in the cup 3 that will not be filled. The first portion 14 of the removal instrument 1 is structured to fit into one of the empty scallop-shaped recesses 9 of the shell 3 such that it has access to the side (outer surface 4*b*) of the liner 2 for impaction. The shape, size, and configuration of embodiments of the portions of the engagement structure 19 are further described below in reference to FIGS. 1-9. In some embodiments, the liner and shell have one or more recesses and corresponding structures. In some embodiments, the recesses and structures have different shapes other than scallop-shaped.

The following is a list of certain annotations and components that are described and enumerated in this disclosure in reference to the above-listed figures. However, any aspect, structure, feature or operational function of the devices illustrated in the figures, whether or not named out separately herein, can form a portion of various embodiments of the invention and may provide basis for one or more claim limitation relating to such aspects, with or without additional description. The annotations and enumerated components include:

1 disassembly instrument
2 acetabular liner ("liner")
3 acetabular shell ("shell" or "cup")
4*a* inner surface of liner
4*b* outer surface of the liner
5 outer surface of cup
6 peripheral (top) surface of liner
7 peripheral (top) surface of cup
8 scallop-shaped protrusion of liner
9 scallop-shaped recess of cup
10 proximal end
11 elongated member
12 distal end
13 opening
14 first portion
15 handle
16 second portion
17 longitudinal axis
18 first tapered surface
19 an acetabular liner engagement structure ("engagement structure")
20 second tapered surface
21 opening of the liner
22 first end face
24 second end face
27 inside surface
28 edge
30 bevel
32 bottom surface
34 top surface
36 outer edge, first end face
38 inner edge, first end face
40 outer edge, second end face
42 inner edge, second end face
44 outer surface, first portion
45 inner surface, first portion
46 outer surface, second portion
47 inner surface, second portion
48 length first portion
50 length second portion
52 lateral length of opening
53 width of opening
54 width of first portion
56 width of second portion
58 proximal end of engagement structure
60 distal end of engagement structure
62 liner rim Illustrative Examples of Device for Assembling Implant Systems Turning now to the figures, FIG. 1 illustrates an example of two disassembly instruments 1*a* and 1*b* positioned to separate an acetabular liner 2 from a shell 3, the acetabular liner 2 being positioned inside the shell 3. The liner 2 has an inner surface 4*a*, an outer surface 4*b* (FIG. 2), and a peripheral top surface 6. The shell 3 has an outer surface 5, an inner surface (not shown), and a peripheral top surface 7. The outer surface 4*b* of the liner 2 is positioned adjacent to the inner surface of the shell 3 when the liner 2 is coupled to the shell 3.

The disassembly or removal instrument ("instrument") 1 has a proximal end 10 and a distal end 12. In this example, the instruments 1*a* and 1*b* include an elongated member 11 between the proximal end 10 and distal end 12, an engagement structure 19 positioned on the proximal end 10, and a handle 15 positioned on the distal end 12. The elongated member 11 includes a top surface 34 and a bottom surface 32. The engagement structure 19 includes a first portion 14 and a second portion 16 which are illustrated in further detail in FIGS. 2 and 4-9.

Figure 2:
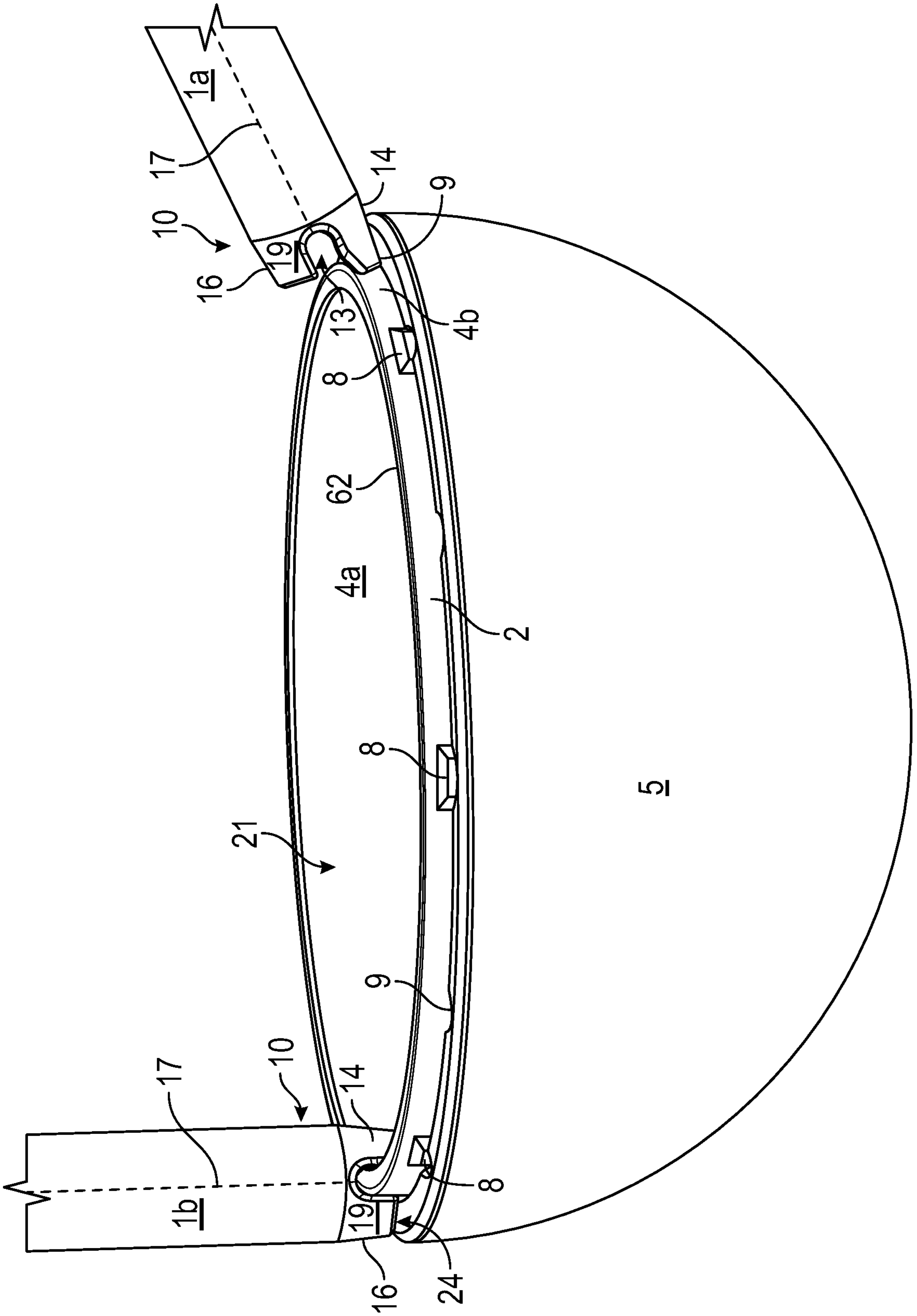
FIG. 2 is a perspective view of proximal ends the first and second instruments illustrated in FIG. 1 that are positioned to separate an acetabular liner from a shell.

FIG. 2 is a perspective view illustrating proximal ends 10 of the two instruments 1*a* and 1*b* illustrated in FIG. 1, the instruments 1*a*, 1*b* positioned to separate the liner 2 from the shell 3. Although two instruments are illustrated and could be used together (e.g., by two different people), the instruments 1*a* and 1*b* are more often, or always, used one at a time. Accordingly, the figures that illustrate two disassembly instruments may be thought of as illustrating two different instances of using the same instrument. Each of the instruments 1*a*, 1*b* has a longitudinal axis 17. The shell 3 includes a plurality of scallop-shaped recesses 9 positioned in the peripheral top surface 7 of the shell 3. In some embodiments, the recesses can be other shapes. The illustrated example liner 2 includes two or more scallop-shaped protrusions 8 that are sized to fit into the recesses 9. Other metal liners can have zero protrusions.

Figure 4:
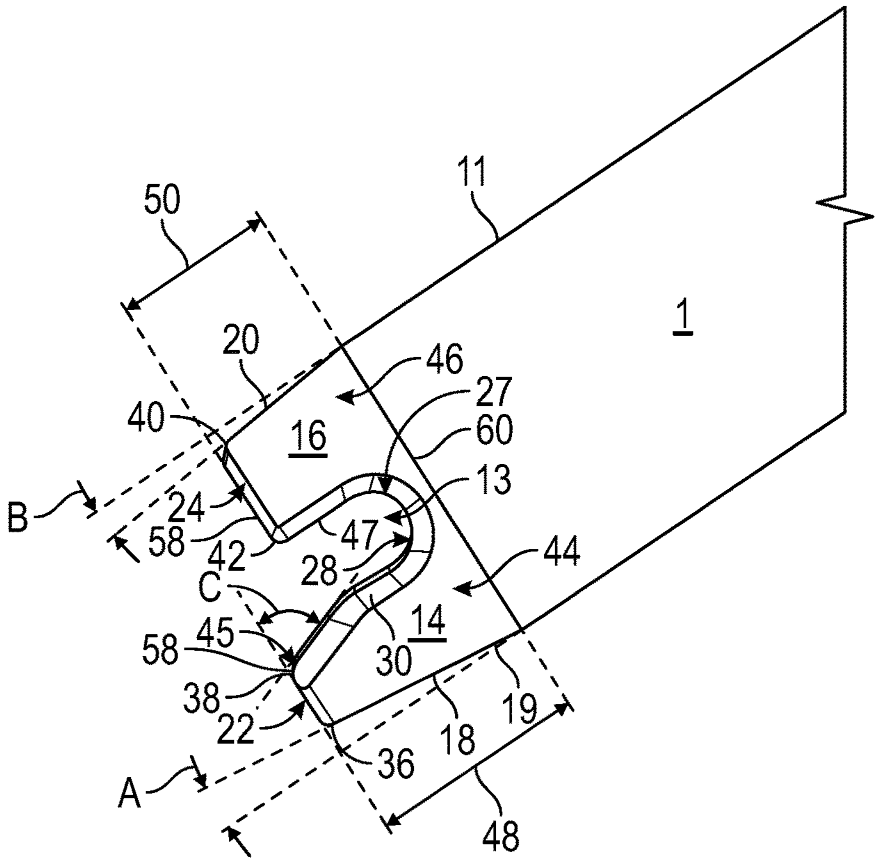
FIG. 4 illustrates an elevation view of the proximal end of the disassembly instrument illustrated in FIGS. 1-3.
Figure 5:
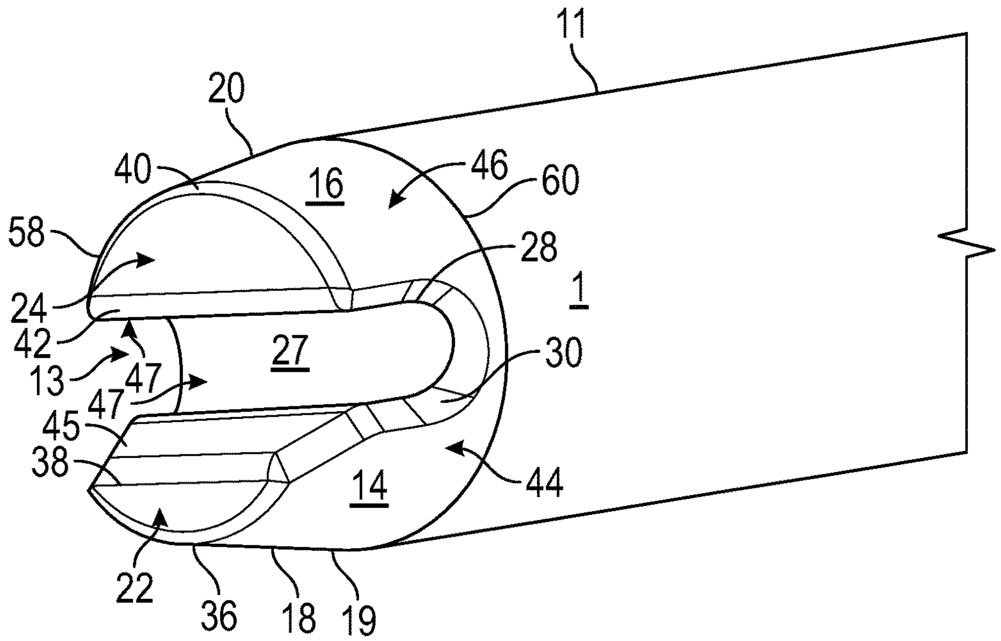
FIG. 5 illustrates a perspective view of the left-side proximal end of the disassembly instrument illustrated in FIGS. 1-4.

A first portion 14 of the engagement structure 19 of instrument 1*a*, shown on the right-hand side of FIG. 2, is positioned in a scallop-shaped recess 9 of the shell 3 with surface of the first portion 14 adjacent to the outer surface 5 of the shell 3. An opening 13 in the engagement structure 19 separates the first portion 14 from the second portion 16. A second instrument 1*b*, shown on the left-hand side of FIG. 2, where the first portion 14 of instrument 1*b* is positioned adjacent to the inner surface 4*a* of the liner 2. The relative location of the instrument on the cup is not important, just that it contacts the peripheral top surface 7 of the cup 3. The second portion 16 of the instrument 1*b* is positioned adjacent to the top surface 7 of the shell 3. The engagement structure 19 is configured to allow the rim 62 of the liner 2 to extend into the opening 13 when the instrument 1*b* is positioned as shown, allowing a second end face 24 of the second portion 16 to contact the top surface 7 of the shell 3, while the first portion 14 extends into the opening 4*a* of the liner 2. Further details of the configuration of engagement structure 19 are illustrated in FIGS. 4 and 5. The lateral length 52 (FIG. 6) and the height 53 (FIG. 6) of the opening 13 are sized to allow the rim 62 of the liner 2 to extend into the opening 13, as illustrated in FIGS. 1 and 2.

Figures 3A, 3B, 3C, 3D:
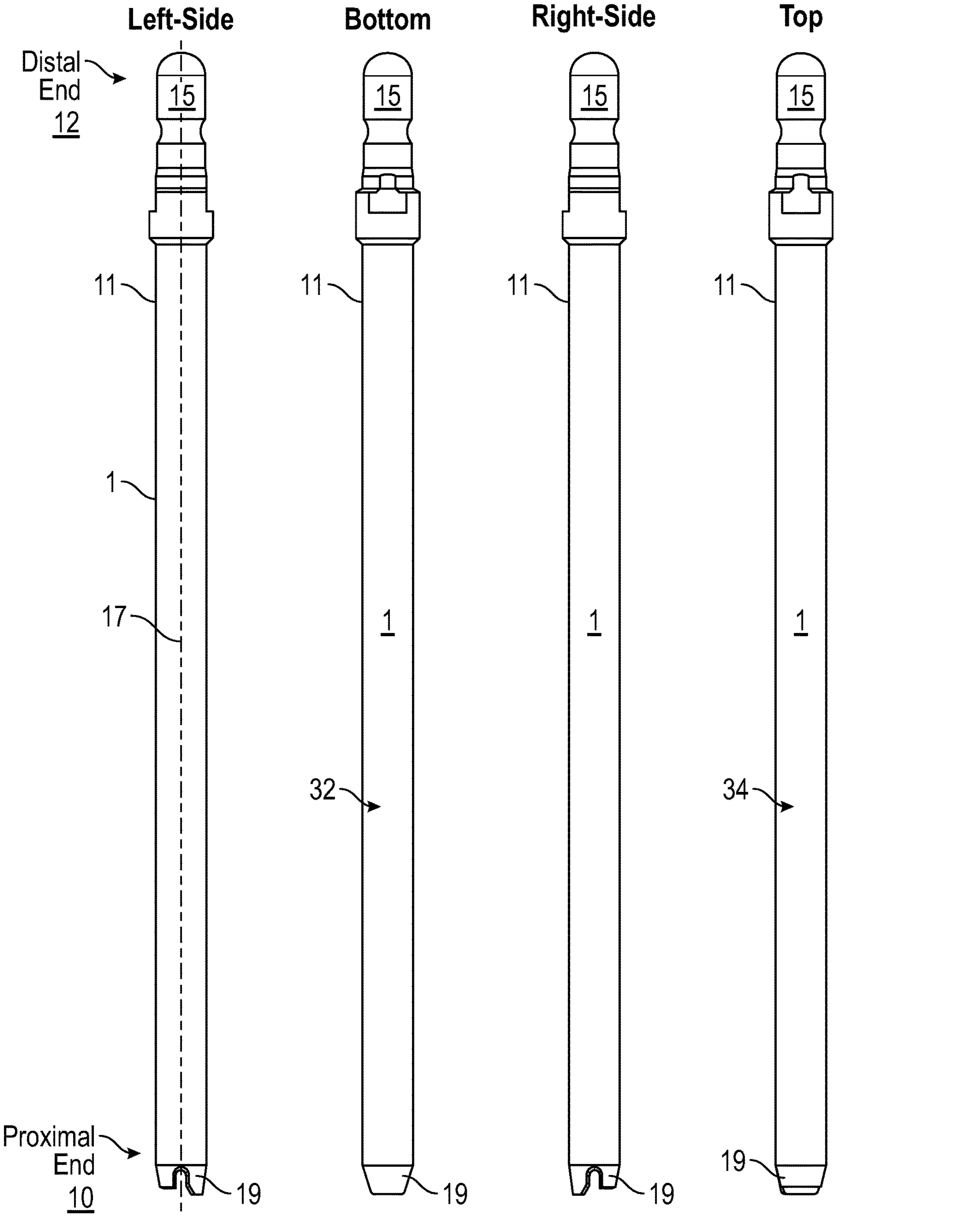
FIG. 3A-3D illustrate elevation views of an example of a disassembly instrument, where

FIG. 3A-3D illustrate elevation views of four sides of an example of a disassembly instrument 1. FIG. 3A shows a left-side elevation view of the disassembly instrument 1. FIG. 3B shows the bottom-side elevation view of the disassembly instrument 1. FIG. 3C shows the right-side elevation view of the disassembly instrument 1. FIG. 3D shows a top elevation view of the disassembly instrument 1. In the embodiments illustrated herein, the elongated member 11 is cylindrical-shaped, having a circular cross-section. However, in other embodiments, the cross-section of the elongated member 11 can be, for example, oval, square, rectangular, pentagonal, hexagonal, octagonal, or be of any other shape.

Referring now to FIGS. 4 and 5, FIG. 4 illustrates a left-side elevation view of the proximal end of the example of the disassembly instrument 1 illustrated in FIGS. 1-3. FIG. 5 illustrates a left-side perspective view of the proximal end 10 of the disassembly instruments 1 illustrated in FIGS. 1-4. The engagement structure 19 extends from a distal end 60 of the engagement structure 19 to a proximal end 58. The engagement structure 19 includes the first portion 14 that extends a length 48 from the distal end 60 of the engagement structure to a first end face 22. The first portion 14 includes a curved outer surface 44. In this example, the second portion 16 includes a curved outer surface 46. In some embodiments, the second portion does not necessarily need to include a curved surface but instead have a different shape. In some embodiments, the second portion includes a curved surface for ease of manufacturing, as well as other reasons. In some embodiments, the length 48 of the first portion 14 is between about 4 mm and about 9 mm. In some embodiments, the length 48 of the first portion 14 is about 6 mm, plus or minus 1 mm. The engagement structure 19 also includes the second portion 16 that extends a length 50 from the distal end 60 of the engagement structure to a second end face 24. In some embodiments, the length 50 of the second portion is between about 2 mm and about 6 mm. In some embodiments, the length 50 of the second portion is about 3.5 mm, plus or minus 1 mm.

In some preferred embodiments, the first end portion 14 includes a first tapered surface 18 such that the first portion 14 tapers inward as it extends from the distal end 60 to the first end face 22. In some embodiments, the first end portion 14 does not taper inward but instead extends aligned with the angle of a surface of the elongated member 11. In some embodiments, the first portion 14 tapers inward at an angle A of between about 0 degrees and about 20 degrees. For example, in some embodiments, the first portion 14 tapers inward at an angle A of 1, 2, 3, 4, 5, 6, 7, 8, 9, 10, 11, 12, 13, 14, 15, 16, 17, 18, 19, or 20 degrees, plus or minus 0.5 degrees. In some embodiments, the first portion 14 tapers inward at an angle A of between about 5 degrees and about 11 degrees. In some embodiments, the first portion 14 tapers inward at an angle A of between about 7 degrees and about 9 degrees.

In some embodiments, including in some preferred embodiments, the second end portion 16 includes a second tapered surface 20 such that the second portion 16 tapers inward as it extends from the distal end 60 to the second end face 24. In some embodiments, the second end portion 16 does not taper inward but instead extends aligned with the angle of a surface of the elongated member 11. In some embodiments, the second portion 16 tapers inward at an angle B of between about 0 degrees and about 20 degrees. For example, in some embodiments, the second portion 16 tapers inward at an angle B of 1, 2, 3, 4, 5, 6, 7, 8, 9, 10, 11, 12, 13, 14, 15, 16, 17, 18, 19, or 20 degrees, plus or minus 0.5 degrees. In some embodiments, the second portion 16 tapers inward at an angle B of between about 3 degrees and about 9 degrees. In some embodiments, the second portion 16 tapers inward at an angle B of between about 6 degrees and about 8 degrees. In some embodiments, the second portion 16 has an outward “taper” such that the second portion 16 angles outward at an angle of between about 0 degrees and about 20 degrees. For example, in some embodiments, the second portion 16 tapers outward at an angle of 1, 2, 3, 4, 5, 6, 7, 8, 9, 10, 11, 12, 13, 14, 15, 16, 17, 18, 19, or 20 degrees, plus or minus 0.5 degrees.

In some embodiments, the first end face 22 extends from an outer edge 36 to an inner edge 38. In some embodiments, first end face 22 is aligned at or about perpendicular to the longitudinal axis 17. In some embodiments, the first portion 14 also includes an inner surface 45 that angles inward from the inner edge 38 to an inside surface 27, at an angle C with respect to the first face 22, the inside surface 27 facing the opening 13. In some embodiments, angle C is between 30 degrees and 88 degrees. In some preferred embodiments, angle C is between 50 degrees and 80 degrees. For example, in some embodiments angle C is 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 degrees, plus or minus 0.5 degrees. The inside surface 27 can be curved (as illustrated) and bounded by an edge 28. In some embodiments, the edge 28 includes a bevel 30 (e.g., a beveled edge). In some embodiments, the first portion 14 also includes an inner surface 45 that angles inward from the inner edge 38 to an inside surface which is not curved, for example, rectangular (e.g., having one or more squared or non-curved corners) which faces the opening 13. In such embodiments, the edge 28 can include a bevel 30 (e.g., a beveled edge).

In some embodiments, the second end face 24 extends from an outer edge 40 to an inner edge 42. In some embodiments, second end face 24 is aligned at or about perpendicular to the longitudinal axis 17. In some embodiments, the second portion 16 also includes an inner surface 47 that extends from the inner edge 42 to the curved inside surface 27. The curved inside surface 27 extending on the second portion 16 is bounded by edge 28. In some embodiments, the edge 28 includes a bevel 30 (e.g., a beveled edge).

Figure 6:
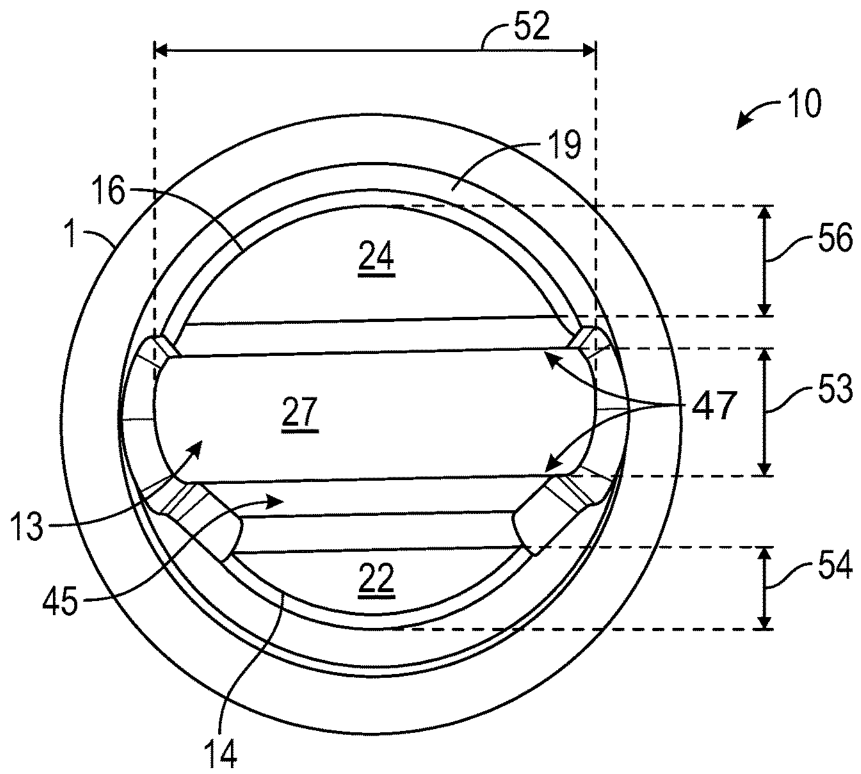
FIG. 6 illustrates an elevation view of the end of proximal end of the disassembly instrument illustrated in FIG. 1-5.

FIG. 6 illustrates an elevation view of the end of proximal end 10 of the disassembly instrument 1 illustrated in FIG. 5. In some embodiments, the first end face 22 extends a width 54 of about 1 mm and about 6 mm. For example, a width of 1 mm, 2 mm, 3 mm, 4 mm, 5 mm, or 6 mm, plus or minus 0.5 mm. In some embodiments, the second end face 24 extends a width 56 of between about 1 mm and about 10 mm. For example, a width of 1 mm, 2 mm, 3 mm, 4 mm, 5 mm, 6 mm, 7 mm, 8 mm, 9 mm, or 10 mm, plus or minus 0.5 mm. The opening 13 extends laterally across the acetabular engagement structure 19, having a lateral length dimension 52. The opening 13 has a height dimension 53, that extends from the inner surface 47 of the first portion 14 to the inner surface 47 of the second portion 16. The height dimension 53 is larger than the thickness of the rim 62 of the liner 2 to allow the curved liner rim 62 to extend into the opening 13. In some embodiments, the height dimension 53 is between 2 mm and 30 mm. For example, the height dimension may be, or be between any two of, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm, plus or minus 0.5 mm. In some embodiments, the height dimension 52 is between 5 mm and 15 mm. For example, the height dimension may be, or be between any two of, 5 mm, 6 mm, 7 mm, 8 mm, 9 mm, 10 mm, 11 mm, 12 mm, 13 mm, 14 mm, or 15 mm, plus or minus 0.5 mm. In some embodiments, the lateral length dimension 52 is between 10 mm and 90 mm. In some embodiments, the lateral length dimension 52 is between 30 mm and 70 mm. For example, the lateral length dimension may be, or be between any two of, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, or 90 mm, plus or minus 0.5 mm.

Figure 7:
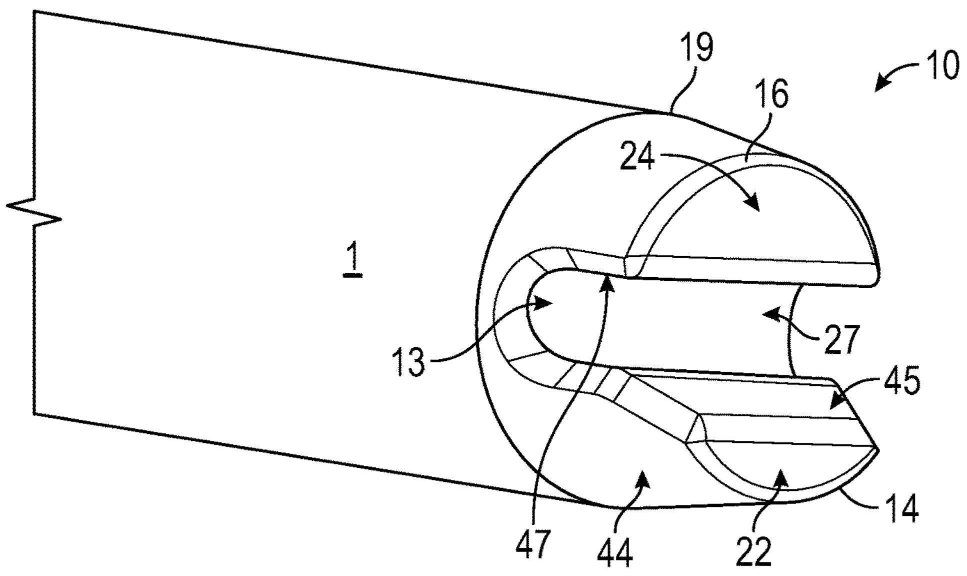
FIG. 7 illustrates a perspective view of the right-side proximal end of the disassembly instrument illustrated in FIGS. 1-6.

FIG. 7 further illustrates the proximal end of the instrument 1 showing a perspective view of the right-side proximal end of the embodiment of the engagement structure 19, illustrated in FIGS. 1-9.

Figure 8:
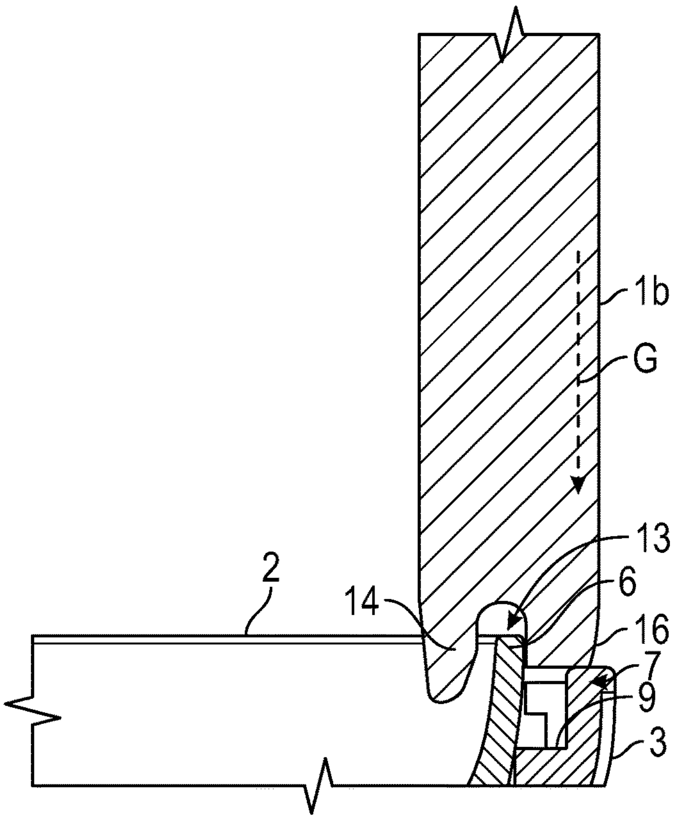
FIG. 8 illustrates the proximal end of the disassembly instrument engaged with the liner and shell, where a first portion of the engagement structure of the instrument is positioned inside the liner and a second portion of the engagement structure of the instrument is positioned on the outside of the liner with the end-face of the second portion adjacent to the top surface of the shell.
Figure 9:
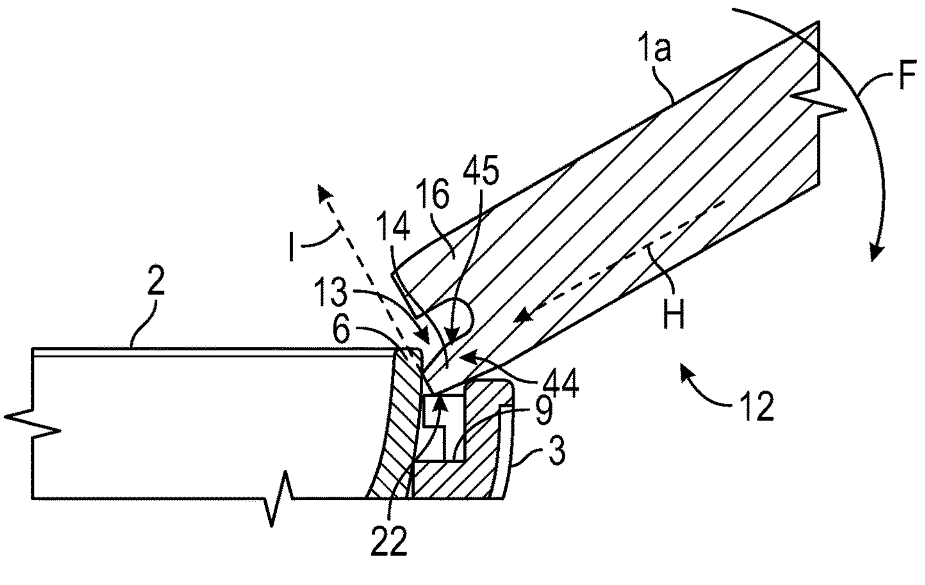
FIG. 9 illustrates the proximal end of the disassembly instrument engaged with the liner and shell, where a first portion of the engagement structure of the instrument is positioned outside of the liner in a recess of the shell with an inner surface of the first portion in contact with the outside surface of the liner and an outer surface of the first portion in contact with the shell, such that the disassembly instrument can provide an impact/shock to the liner to decouple the liner from the shell. In another use example, the handle is moved downward (with respect to the orientation of the figure) such that the first portion applies an upward force (with respect to the orientation of the figure) to disengage the liner from the shell.

FIG. 8 and FIG. 9 further illustrate the engagement structure 19 engaged with the liner 2 and the shell 3 to separate the liner 2 from the shell 3. In FIG. 8, a first portion 14 of the engagement structure 19 is positioned in an interior portion of the liner 2. As illustrated in FIG. 8, the top surface 6 of the liner 2 extends into the opening 13. A second portion 16 of the engagement structure 19 is positioned in contact with the outside of the shell 3, with the second end-face 24 of the second portion 16 positioned adjacent to, and in contact with, the top surface 7 of the shell to allow a force illustrated by the dashed arrow G (e.g., a downward force in reference to the orientation of FIG. 8) to be applied to the shell 3 without applying a downward force to the liner 2.

FIG. 9 illustrates the engagement structure 19 of the disassembly instrument 1 engaged with the liner 2 and shell 3. A first portion 14 of the engagement structure 19 is positioned outside of the liner 2 in a recess 9 of the shell 3 with an inner surface 45 and/or the first end-face 22 in contact with the outside surface of the liner 2 and an outer surface 44 of the first portion 14 in contact with the shell 3. In this arrangement, the distal end 12 of the instrument 1 can be used to apply a force, illustrated by the dashed arrow H, to the liner 2 (e.g., by applying an impact force to the distal end of the instrument 1, e.g., the handle 15) to separate the liner 2 from the shell 3. Also, a downward force F (with respect to the orientation of the figure) may be applied to the distal end 12 of the instrument 1 such that the first portion 14 applies an upward force (with respect to the orientation of the figure) illustrated by the dashed arrow Ito disengage the liner 2 from the shell 3.

Examples of a Device for Disassembling Implant Systems

Some, but not all, examples of embodiments of a device for disassembling implant systems, are listed below.

Embodiment 1: A disassembly device for separating a hard bearing acetabular liner positioned in, and coupled to, a shell, the disassembly device comprising: an elongated member having a distal end and a proximal end, and a longitudinal axis extending between the distal end and the proximal end; an engagement structure at the proximal end of the elongated member, the engagement structure having a frustum-shaped outer surface the engagement structure comprising a first portion and a second portion separated by an opening defined in-part by a curved inside surface having a distal portion, the first portion comprising a curved outer surface extending a first length from the proximal end of the elongated member, a first end face aligned substantially perpendicular with respect to the longitudinal axis, and an inner surface extending from the first end face to the curved inside surface wherein the first portion is structured to fit at least partially into a scallop-shaped recess on a peripheral top surface of the acetabular shell; a second portion comprising a curved outer surface extending a second length from the proximal end of the elongated member where the second length is less than the first length, a second end face aligned substantially perpendicular with respect to the longitudinal axis, and an inner surface aligned substantially perpendicular to the second face and extending from the second end face to the curved inside surface.

Embodiment 2: The disassembly device of embodiment 1, wherein the first portion is structured and sized to fit at least partially into a scallop-shaped recess on a peripheral top surface of the acetabular shell.

Embodiment 3: The disassembly device of embodiment 1 or 2, wherein the first end-face is hemispherical-shaped.

Embodiment 4: The disassembly device of any one of embodiments 1-3, wherein the second end-face is hemispherical-shaped.

Embodiment 5: The disassembly device of any one of embodiments 1-4, wherein the frustum-shaped outer surface tapers inward at an angle A relative to the longitudinal axis as it extends away from the proximal end of the elongated member, wherein angle A is between about 0 and about 20 degrees.

Embodiment 6: The disassembly device of embodiment 5, wherein angle A is between about 5 degrees and about 11 degrees.

Embodiment 7: The disassembly device of any one of embodiments 1-6, wherein the inner surface extends at an angle C which is between about 30 degrees and about 88 degrees.

Embodiment 8: The disassembly device of embodiment 7, wherein angle C is between about 50 degrees and about 80 degrees.

Embodiment 9: The disassembly device of any one of embodiments 1-8, wherein the first length is between about 4 mm and about 9 mm.

Embodiment 10: The disassembly device of any one of embodiments 1-9, wherein the first length is about 6 mm, plus or minus 1 mm.

Embodiment 11: The disassembly device of any one of embodiments 1-10, wherein the second length is between about 2 mm and about 7 mm.

Embodiment 12: The disassembly device of any one of embodiments 1-11, wherein the second length is about 3.5 mm, plus or minus 1 mm.

Embodiment 13: The disassembly device of any one of embodiments 1-12, wherein the curved inside surface is U-shaped.

Embodiment 14: The disassembly device of embodiment 3, wherein the first end-face surface includes a straight edge and a curved edge, and the straight edge of the first end-face surface is between about 4.5 mm and about 6.6 mm in length.

Embodiment 15: The disassembly device of embodiment 4, wherein the second end-face surface includes a straight edge and a curved edge, and the straight edge of the second end-face surface is between about 3 mm and about 5 mm in length.

Embodiment 16: The disassembly device of any one of embodiments 1-15, further comprising a handle positioned on the distal end of the elongated member.

Embodiment 17: The disassembly device of embodiment 1, wherein the elongated member is a rod having a circular cross-sectional area.

Embodiment 18: The disassembly device of embodiment 1, wherein the acetabular liner comprises metal.

Embodiment 19: The disassembly device of embodiment 1, wherein the acetabular liner comprises ceramic.

Embodiment 20: A disassembly device for separating a hard bearing acetabular liner positioned in, and coupled to, a shell, the disassembly device comprising: an elongated member having a distal end and a proximal end, and a longitudinal axis extending between the distal end and the proximal end; an engagement structure at the proximal end of the elongated member, the engagement structure comprising a first portion and a second portion separated by an opening, the first portion comprising a curved outer surface extending a first length from the proximal end of the elongated member, a first end face aligned substantially perpendicular with respect to the longitudinal axis, wherein the first portion is structured to fit at least partially into a scallop-shaped recess on a peripheral top surface of the acetabular shell; a second portion comprising an outer surface extending a second length from the proximal end of the elongated member, a second end face aligned substantially perpendicular with respect to the longitudinal axis, and wherein the second portion is structured to contact the top surface of the acetabular shell; and an opening separating the first and second portion comprising inner surfaces extending from first end face and second end face to the inside surface, wherein the opening is structured to accept the top surface of the acetabular liner and allowing the first portion of the device to be positioned within the inner surface of the liner, while the second portion is contact with the top surface of the acetabular shell, without contacting the liner.

Embodiment 21: The disassembly device of embodiment 20, wherein the liner comprises metal or ceramic.

Embodiment 22: A method of separating a liner from an acetabular shell, the method comprising: providing a disassembly tool, the disassembly tool including an elongated member having a distal end and a proximal end, and a longitudinal axis extending between the distal end and the proximal end; an engagement structure at the proximal end of the elongated member, the engagement structure comprising a first portion and a second portion separated by an opening, the first portion comprising a curved outer surface extending a first length from the proximal end of the elongated member, and a first end face aligned substantially perpendicular with respect to the longitudinal axis, and the second portion comprising an outer surface extending a second length from the proximal end of the elongated member, and a second end face aligned substantially perpendicular with respect to the longitudinal axis, and wherein the second portion is structured to contact the top surface of the acetabular shell; and an opening separating the first and second portion, the opening defined by an inner surface extending from first end face and second end face; positioning the top surface of the acetabular liner in the opening with the first portion of the device positioned adjacent to an inner surface of the liner and the second portion is contact with the top surface of the acetabular shell without contacting the liner; and providing a sudden force on the distal end of the elongated member along the longitudinal axis in the direction of the proximal end to at least partially separate the shell from the liner.

Implementation Considerations

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

It will also be understood that, when a feature or element (for example, a structural feature or element) is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value indicated to be "about" may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10" and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A disassembly device for separating a hard bearing acetabular liner positioned in, and coupled to, a shell, the disassembly device comprising:

an elongated member having a distal end and a proximal end, and a longitudinal axis extending between the distal end and the proximal end;

an engagement structure at the proximal end of the elongated member comprising a first portion and a second portion separated by an opening defined in-part by a curved inside surface having a distal portion, the first portion comprising a curved outer surface extending a first length from the proximal end of the elongated member, a first end face aligned substantially perpendicular with respect to the longitudinal axis, and an inner surface extending from the first end face to the curved inside surface;

a second portion comprising a curved outer surface extending a second length from the proximal end of the elongated member where the second length is less than the first length, a second end face aligned substantially perpendicular with respect to the longitudinal axis, and an inner surface aligned substantially perpendicular to the second face and extending from the second end face to the curved inside surface.

2. The disassembly device of claim 1, wherein the first portion is structured and sized to fit at least partially into a scallop-shaped recess on a peripheral top surface of the acetabular shell.

3. The disassembly device of claim 1, wherein the first end-face is hemispherical-shaped.

4. The disassembly device of claim 3, wherein the first end-face surface includes a straight edge and a curved edge, and the straight edge of the first end-face surface is between about 4.5 mm and about 6.6 mm in length.

5. The disassembly device of claim 3, wherein the first end-face surface includes a straight edge and a curved edge, and the straight edge of the first end-face surface is between about 4.5 mm and about 6.6 mm in length.

6. The disassembly device of claim 1, wherein the second end-face is hemispherical-shaped.

7. The disassembly device of claim 6, wherein the second end-face surface includes a straight edge and a curved edge, and the straight edge of the second end-face surface is between about 3 mm and about 5 mm in length.

8. The disassembly device of claim 1, wherein the frustum-shaped outer surface tapers inward at an angle A relative to the longitudinal axis as it extends away from the proximal end of the elongated member, wherein angle A is between about 0 and about 20 degrees.

9. The disassembly device of claim 8, wherein angle A is between about 5 degrees and about 11 degrees.

10. The disassembly device of claim 1, wherein the inner surface extends at an angle C which is between about 30 degrees and about 88 degrees.

11. The disassembly device of claim 10, wherein angle C is between about 50 degrees and about 80 degrees.

12. The disassembly device of claim 1, wherein the first length is between about 4 mm and about 9 mm.

13. The disassembly device of claim 1, wherein the first length is about 6 mm, plus or minus 1 mm.

14. The disassembly device of claim 1, wherein the second length is between about 2 mm and about 7 mm.

15. The disassembly device of claim 1, wherein the second length is about 3.5 mm, plus or minus 1 mm.

16. The disassembly device of claim 1, wherein the curved inside surface is U-shaped.

17. The disassembly device of claim 1, wherein the acetabular liner comprises metal or ceramic.

18. A disassembly device for separating a hard bearing acetabular liner positioned in, and coupled to, a shell, the disassembly device comprising:

an elongated member having a distal end and a proximal end, and a longitudinal axis extending between the distal end and the proximal end;

an engagement structure at the proximal end of the elongated member, the engagement structure comprising a first portion and a second portion separated by an opening, the first portion comprising a curved outer surface extending a first length from the proximal end of the elongated member, a first end face aligned substantially perpendicular with respect to the longitudinal axis;

a second portion comprising an outer surface extending a second length from the proximal end of the elongated member, a second end face aligned substantially perpendicular with respect to the longitudinal axis, and wherein the second portion is structured to contact the top surface of the acetabular shell; and an opening separating the first and second portion comprising inner surfaces extending from first end face and second end face to the inside surface, wherein the opening is structured to accept the top surface of the acetabular liner and allowing the first portion of the device to be positioned within the inner surface of the liner, while the second portion is contact with the top surface of the acetabular shell, without contacting the liner.

19. The disassembly device of claim 18, wherein the liner comprises metal or ceramic.

20. A method of separating a liner from an acetabular shell, the method comprising:

providing a disassembly tool, the disassembly tool including an elongated member having a distal end and a proximal end, and a longitudinal axis extending between the distal end and the proximal end;

an engagement structure at the proximal end of the elongated member, the engagement structure comprising a first portion and a second portion separated by an opening, the first portion comprising a curved outer surface extending a first length from the proximal end of the elongated member, and a first end face aligned substantially perpendicular with respect to the longitudinal axis, and the second portion comprising an outer surface extending a second length from the proximal end of the elongated member, and a second end face aligned substantially perpendicular with respect to the longitudinal axis, and wherein the second portion is structured to contact the top surface of the acetabular shell; and an opening separating the first and second portion, the opening defined by an inner surface extending from first end face and second end face;

positioning the top surface of the acetabular liner in the opening with the first portion of the device positioned adjacent to an inner surface of the liner and the second portion is contact with the top surface of the acetabular shell without contacting the liner; and providing a sudden force on the distal end of the elongated member along the longitudinal axis in the direction of the proximal end to at least partially separate the shell from the liner.

* * * * *